(12) United States Patent  
Roy et al.

(10) Patent No.: US 8,545,524 B2
(45) Date of Patent: Oct. 1, 2013

(54) METHOD AND DEVICE FOR INTERCONNECTION OF TWO TUBULAR ORGANS

(75) Inventors: Sumit Roy, Olso (NO); Erik Fosse, Oslo (NO); Ole Jakob Elle, Oslo (NO)

(73) Assignee: Anastomosis AS, Stavanger (NO)

( * ) Notice: Subject to any disclaimer, the term of this patent is extended or adjusted under 35 U.S.C. 154(b) by 912 days.

(21) Appl. No.: 10/522,815

(22) PCT Filed: Jul. 25, 2003

(86) PCT No.: PCT/NO03/00258
§ 371 (c)(1),
(2), (4) Date: Oct. 21, 2005

(87) PCT Pub. No.: WO2004/010898
PCT Pub. Date: Feb. 5, 2004

(65) Prior Publication Data
US 2006/0100648 A1 May 11, 2006

(30) Foreign Application Priority Data

Jul. 29, 2002 (NO) .................................. 20023605

(51) Int. Cl.
*A61B 17/11* (2006.01)
(52) U.S. Cl.
USPC ....................................................... 606/153
(58) Field of Classification Search
USPC .................. 606/151–158, 139, 142–148; 623/1.11–1.15; 285/267, 316, 317, 319, 285/285/34, 35, 214, 216, 67, 140.1, 249, 285/255, 257, 258, 382, 136.1–143.1, 210
See application file for complete search history.

(56) References Cited

U.S. PATENT DOCUMENTS

| 522,005 A | * | 6/1894 | Burke | .......................... 285/210 |
| 1,339,620 A | * | 5/1920 | Hart | ....................... 285/148.14 |
| 2,211,776 A | * | 8/1940 | Haury | .......................... 285/231 |

(Continued)

FOREIGN PATENT DOCUMENTS

| EP | 455036 | 11/1991 |
| EP | 0723766 | 7/1996 |

(Continued)

OTHER PUBLICATIONS

Heijmen, R.H. et al., "A Novel One-Shot Anastomotic Stapler Prototype for Coronary Bypass Grafting on the Beating Heart: Feasibility in the Pig", *Thoracic Cardiovascular Surgery*, 1999, 117: 117-125.

*Primary Examiner* — Kathleen Holwerda
(74) *Attorney, Agent, or Firm* — Young & Thompson

(57) ABSTRACT

A method for interconnection of two tubular organs via an opening at one end of an end portion of a first organ and an aperture in a side wall of a second organ. The end portion is initially passed through a first passage of a first element until the end portion projects past an end edge of the element, whereupon the end portion is everted round the end edge. Gripping parts of a second element with a second passage are then inserted in the second organ via the aperture. Finally, the first element with the everted portion of the first organ is inserted in the second passage, whereby the gripping parts are influenced in such a manner that they come into engagement with the inside of an edge portion of the aperture. A device for implementation of the method.

20 Claims, 12 Drawing Sheets

(56) References Cited

U.S. PATENT DOCUMENTS

| | | | | |
|---|---|---|---|---|
| 2,537,183 | A | * | 1/1951 | Bloomer ........................ 285/210 |
| 3,228,713 | A | * | 1/1966 | Frost ............................. 285/109 |
| 3,358,357 | A | * | 12/1967 | Defauw .......................... 29/510 |
| 3,908,662 | A | * | 9/1975 | Razgulov et al. ............. 606/149 |
| 5,366,462 | A | | 11/1994 | Kaster et al. |
| 5,716,081 | A | * | 2/1998 | Leigh-Monstevens et al. ............................. 285/319 |
| 6,193,734 | B1 | * | 2/2001 | Bolduc et al. ................. 606/153 |
| 6,419,681 | B1 | | 7/2002 | Vargas et al. |
| 6,524,322 | B1 | * | 2/2003 | Berreklouw ................... 606/153 |
| 6,702,828 | B2 | * | 3/2004 | Whayne ......................... 606/153 |

FOREIGN PATENT DOCUMENTS

| | | |
|---|---|---|
| EP | 1149567 | 10/2001 |
| FR | 2737653 | 2/1997 |
| WO | WO 97/27898 | 8/1997 |
| WO | WO 99/62415 | 12/1999 |
| WO | WO 0027311 | 5/2000 |
| WO | WO 00/56228 | 9/2000 |
| WO | WO 00/72764 | 12/2000 |
| WO | WO 01/13820 | 3/2001 |
| WO | WO 0134037 | 5/2001 |
| WO | WO 01/70119 | 9/2001 |
| WO | WO 0170090 | 9/2001 |

* cited by examiner

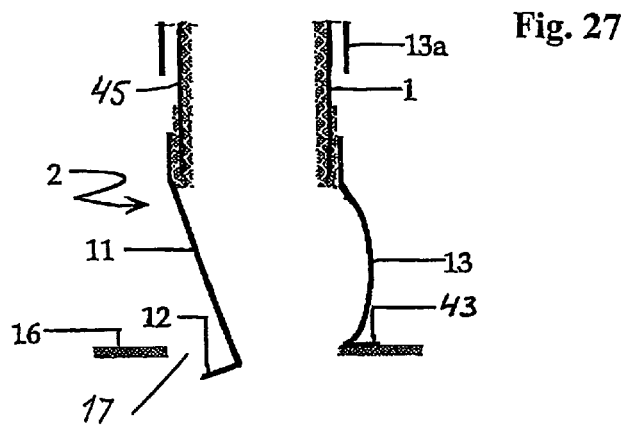
Fig. 27
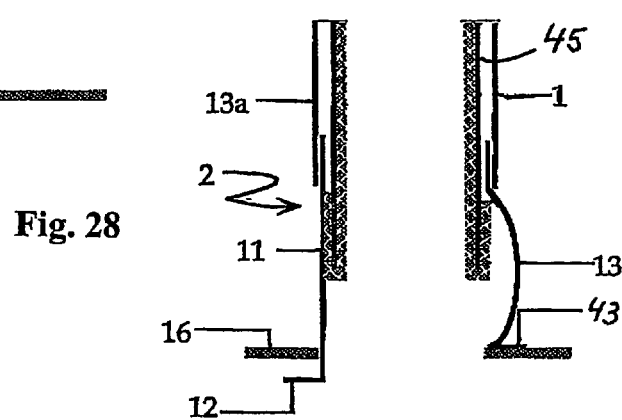
Fig. 28
Fig. 31
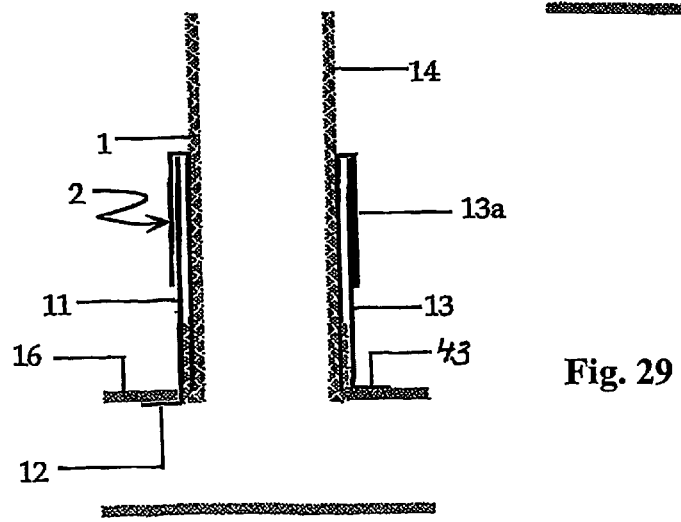
Fig. 29

Fig. 30
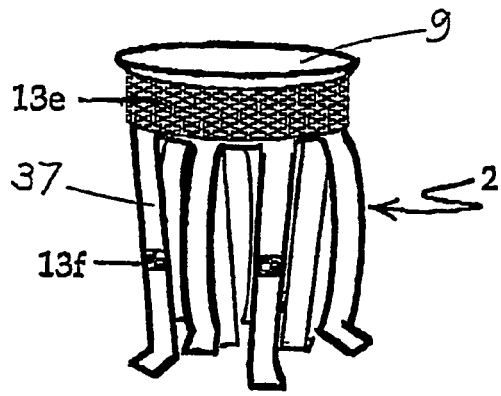
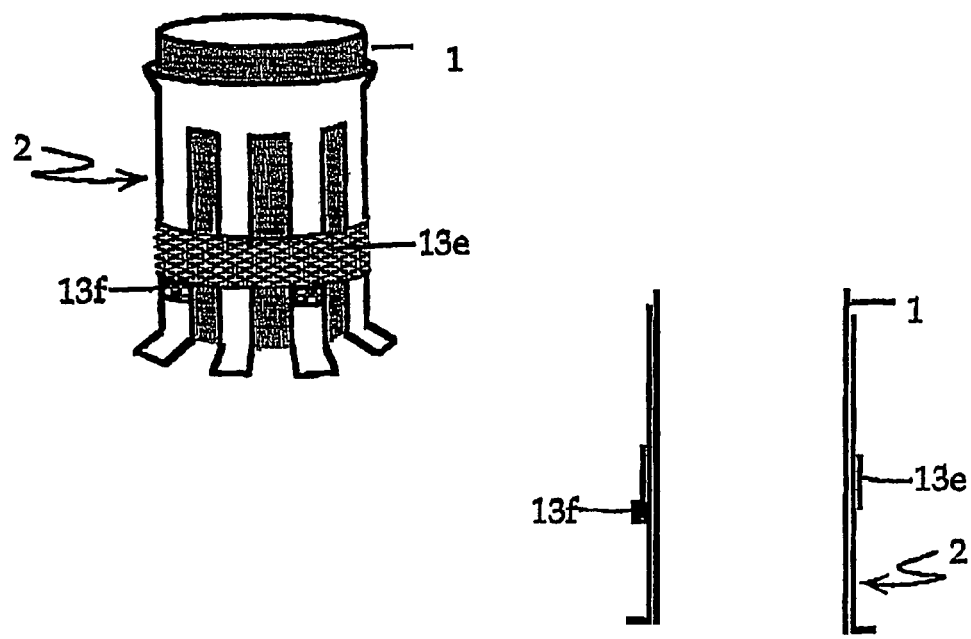
Fig. 32

METHOD AND DEVICE FOR INTERCONNECTION OF TWO TUBULAR ORGANS

BACKGROUND OF THE INVENTION

1. Field of the Invention

The invention relates to a method for interconnection of and fluid communication between two tubular organs via an opening in an end of an end portion of a first organ and an aperture in a side wall of a second organ.

The invention also relates to a device for implementation of the method.

2. Description of the Related Art

Among those skilled in the art an increasing interest in minimally invasive surgery and a general desire to reduce the dependence on individual skills for carrying out operations has led to a need for a new method and a new device for anastomosing (connecting) tubular organs such as blood vessels. In contrast to ordinary operations, in the case of minimally invasive surgery, the access to the organs concerned or the target organs is extremely limited, which makes the use of standard anastomosis techniques based on manual suturing of the organs difficult and in some cases impossible. This difficulty is particularly relevant in the surgical field associated with coronary artery bypass, since an anatomical and physiological idiosyncrasy (hypersensitivity) of the heart results in very little tolerance of mistakes in this area when performing the procedure. Furthermore, the brief period required for anastomosis of blood vessels by suturing in neurovascular and aortic operations has largely prevented the use of less invasive surgical procedures.

Over the years many devices for anastomosis of blood vessels and similar tubular organs and methods for use of such devices have been disclosed in the patent literature.

U.S. Pat. No. 2,127,903 (Bowen)
U.S. Pat. No. 3,155,095 (Brown)
U.S. Pat. No. 3,620,218 (Schmitt et al.)
U.S. Pat. No. 3,683,926 (Suzuki)
U.S. Pat. No. 4,214,586 (Mericle)
U.S. Pat. No. 4,366,819 (Castor)
U.S. Pat. No. 4,368,736 (Castor)
U.S. Pat. No. 4,470,415 (Wozniak)
U.S. Pat. No. 4,675,008 (Tretbar)
U.S. Pat. No. 4,512,761 (Raible)
WO 97/27898 (Evard et al.)
U.S. Pat. No. 4,552,148 (Hardy, Jr. et al.)
U.S. Pat. No. 4,753,236 (Healy)
U.S. Pat. No. 4,769,029 (Patel)
U.S. Pat. No. 4,851,001 (Taheri)
U.S. Pat. No. 4,816,028 (Kapadia et al.)
U.S. Pat. No. 4,957,499 (Lipatov et al.)
U.S. Pat. No. 5,156,691 (Ehrenfeld)
U.S. Pat. No. 5,123,908 (Chen)
U.S. Pat. No. 5,192,289 (Jessen)
U.S. Pat. No. 5,250,058 (Miller)
U.S. Pat. No. 5,222,963 (Brinkerhoff et al.)
U.S. Pat. No. 5,330,490 (Wilk et al.)
U.S. Pat. No. 5,364,389 (Anderson)
U.S. Pat. No. 5,399,352 (Hanson)
U.S. Pat. No. 5,425,738 (Gustafson et al.)
U.S. Pat. No. 5,425,739 (Jessen)
U.S. Pat. No. 5,443,497 (Venbrux)
U.S. Pat. No. 5,445,644 (Pietrafitta et al.)
U.S. Pat. No. 5,456,712 (Maginot)
WO 00/72764 (Stevens et al.)
U.S. Pat. No. 5,456,714 (Owen)
U.S. Pat. No. 5,503,635 (Sauer et al.)
U.S. Pat. No. 5,509,902 (Raulerson)
U.S. Pat. No. 6,179,849 (Yencho et al.)

None of the objects of these publications are employed by skilled people in the field of vascular surgery. New developments in the field, however, offer again indications that anastomosis by means of suturing may soon become obsolete. Even though the new methods and devices represent improvements in relation to those previously used, however, they are all encumbered with drawbacks particularly in connection with minimally invasive surgery.

The device GraftConnector™ (WO 01/13820 (Solem)) comprises a Stents shape for securing the inlet branch to the outlet branch internally in a cavity when performing an anastomosis. Experience with percutaneous Stents shapes, however, raises doubts concerning foreign objects which are left in a blood vessel.

Results reported to date concerning automated suturing with V-Drive™ (Bolduc (WO 99/62415)) have not been promising. The execution of each anastomosis takes an average of 15 minutes and the technique is more difficult than in normal suturing (Martens S. et al. CTT Cardiothoracic Techniques VIII, 2002).

The execution of anastomosis with AutoSutur OneShot™ (U.S. Pat. No. 6,024,748 (Manzo)), while reducing the operating time, also increases the risk of vascular damage, thus cancelling out the benefit (Heijmen R. H. et al., J. Thoracic Cardiovascular Surgery 1999, 117:117-25).

Peripheral hoops (Symmetry™, Corlink™), which are described by Peterson et al. (U.S. Pat. No. 6,152,937), Swanson et al. (U.S. Pat. No. 5,113,621) and Loshakove et al. (LWO/56226, WO 00/56228, WO 01/70119) are not encumbered with the above-mentioned disadvantages.

With these devices, however, barbs are used to attach them to the organs undergoing anastomosis, resulting in a need for the use of complicated, manual operations. In addition to complicating the anastomosis procedure, this limitation actually makes the devices unsuitable for use in remotely controlled (telesurgical) procedures, which will probably replace standard treatment in the coming decades. In addition, the devices have to be made of expensive superelastic alloys, thus preventing widespread use for financial reasons. Thus a need still exists for a simple and inexpensive device which has a long working life, and which permits a rapid and reliable anastomosis of two hollow organs without the use of suturing.

BRIEF SUMMARY OF THE INVENTION

The object of the invention is to provide a method and a device for such an anastomosis which is not encumbered by the above-mentioned drawbacks.

The characteristic of the method and the device according to the invention will be apparent from the characterising features indicated in the claims.

The invention will now be described in greater detail with reference to the drawing which schematically illustrates embodiments of the device according to the invention.

For the sake of simplicity the invention will be explained in connection with blood vessels, but it will be understood that the invention is not limited thereto.

In the following, the directional indication "forwards" should be understood to refer to the direction towards the edge of the pages of the drawings facing the reader, this direction on the drawing corresponding to the direction in which components of the device according to the invention are moved when the components are joined together. Portions of the components and associated objects are similarly indicated. Furthermore, corresponding components of the various embodiments of the invention will be indicated by the same reference numerals.

BRIEF DESCRIPTION OF THE DRAWING FIGURES

FIGS. 27-29 illustrate three simplified longitudinal sections showing respective stages during a connection of the components illustrated in FIG. 25.

FIG. 30 is a perspective view of a seventh embodiment of the external element.

FIG. 31 is a perspective view of an internal element of the first embodiment which has been inserted in an external element of the seventh embodiment.

FIG. 32 illustrates a simplified longitudinal section through the components illustrated in FIG. 31.

DETAILED DESCRIPTION OF THE PREFERRED EMBODIMENTS

In general terms, the device according to the invention comprises a first or internal element 1 and a second or external element 2.

Figure 1:
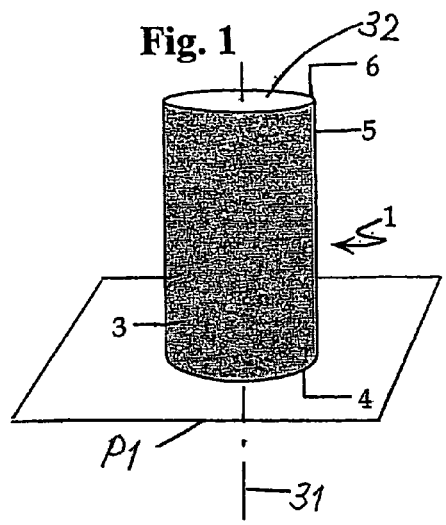
FIG. 1 is a perspective view of a first embodiment of a first or internal element of the device according to the invention.

FIG. 1 illustrates a first embodiment of the first or internal element 1. This element preferably is in the form of a straight, thin-walled, cylindrical sleeve with a circular cross section. The element 1 has a longitudinal axis 31, a front end portion 3, a front end or end edge 4, a rear end portion 5, a rear end or end edge 6 and a first through-going passage 32.

Figure 4:
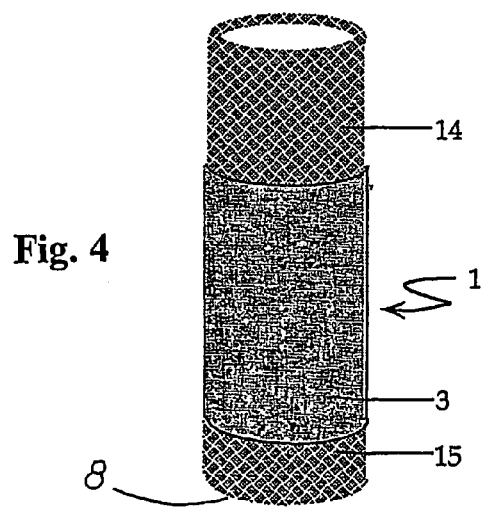
FIG. 4 is a perspective view of a first organ that is inserted in the internal element, where a front end portion of the organ protrudes from the element at a front end thereof.
Figure 5:
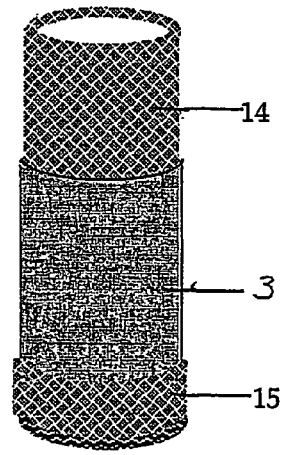
FIG. 5 is a perspective view resembling that illustrated in FIG. 4, but where the front end portion of the organ has been everted around the front end of the internal element.
Figure 6:
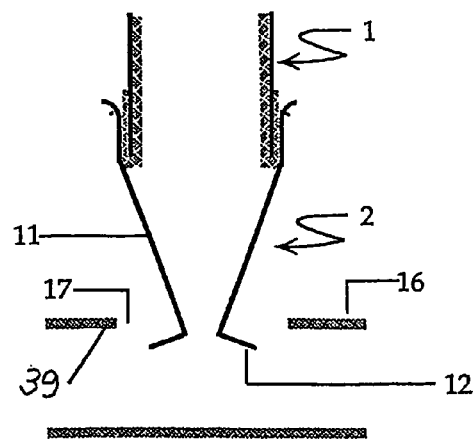
FIG. 6 illustrates a simplified longitudinal section through the internal element carrying the everted, first organ, where a front portion of the internal element has been inserted in a rear portion of an external element according to FIG. 3 and a front portion of the external element has been inserted in an aperture in a side of a second organ.
Figure 7:
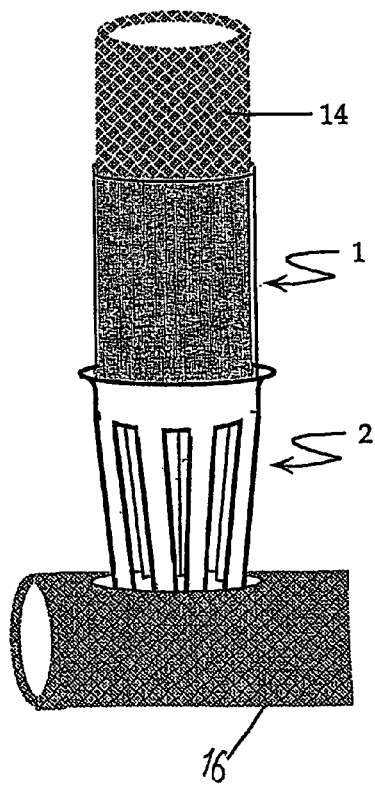
FIG. 7 is a view corresponding to FIG. 6, but where the components are shown in perspective.
Figure 8:
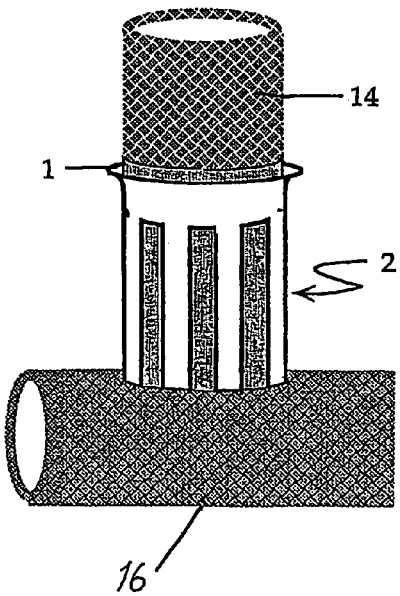
FIG. 8 is a perspective view corresponding to FIG. 7, but where the internal element has been completely inserted in the external element.

As illustrated in FIG. 4 the inner diameter of the internal element 1 is adapted to the outer diameter of a tubular first organ 14 such as a blood vessel. A severed organ 14 with a free end portion 15 with an end edge 8 can therefore be passed through the element 1 until the end portion 15 protrudes from the element 1 at the element's front end 4. The end portion 15 can then be everted or folded round the front end 4 of the element 1 and caused to extend backwards along the outside of the element's front end portion 3, as illustrated in FIG. 5. To prevent the organ from being damaged during the eversion process, the element's front end 4 may be rounded, and to prevent the end portion 15 from being moved back, the front end 4 may be rough.

Figure 2:
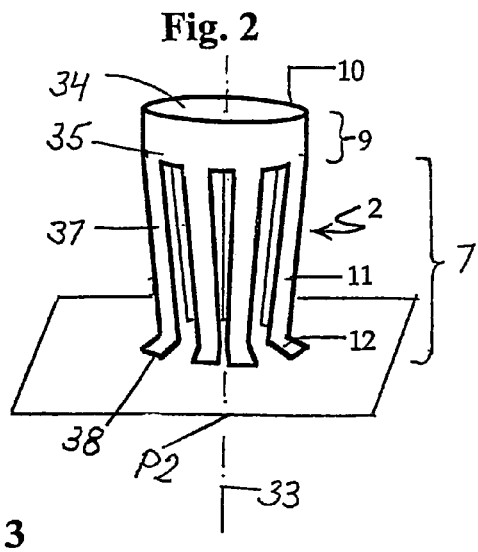
FIG. 2 is a perspective view of a first embodiment of a second or external element of the device according to the invention.

FIG. 2 illustrates a first embodiment of the second or external element 2 of the device. The external element 2 is similarly provided round a longitudinal axis 33 and has a through-going, second passage 34. The external element 2 has a rear, thin-walled, sleeve-shaped end portion or receiving portion 9 with a rear end or edge 10 and a front end or end area 35.

The cross section of the receiving portion 9 of the external element 2 is preferably circular and is adapted to the cross section of the internal element 1 in such a manner that the internal element 1 with the everted blood vessel 14 can be inserted into this receiving portion 9. The internal diameter of the external element 2 hereby corresponds to the external diameter of the internal element 1 plus the double wall thickness of the first organ 14.

To the front end 35 of the receiving portion 9 of the external element 2 is connected a front end portion 7 comprising a number of elongated, first fingers 11 extending or pointing away from the receiving portion 9 and arranged at intervals along the periphery of the receiving portion 9.

The fingers 11 comprise a main portion 37, in front of which are connected gripping claws or parts 12. The main portions 37 hereby extend forwards along and simultaneously radially towards the longitudinal axis 33, thereby forming a small angle with it when they are not influenced by external forces, i.e. when they are relaxed. The gripping claws or parts 12 are bent at an angle relative to the main portion 37 and extend approximately radially away from the longitudinal axis 33. When the fingers 11 are not influenced by external forces, i.e. when they are relaxed, the main portions extend in such a manner that the gripping parts' radially external edges or terminations 38 are located on a closed loop, preferably circular, located on or slightly radially within an axial extension of the receiving portion 9 of the external element 2.

The fingers' main portions 37, however, may be bent elastically radially outwards in the axial plane which comprises the longitudinal axis 33 to a position wherein the main portion 37 extends substantially axially and the gripping parts 12 extend substantially across the longitudinal axis 33 in this embodiment of the internal element 1.

Figure 3:
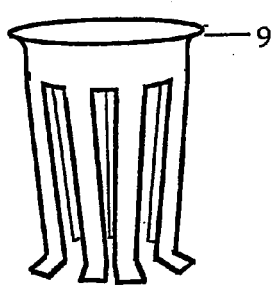
FIG. 3 is a perspective view of a second embodiment of the external element.

FIG. 3 illustrates a second embodiment of the external element 2, where the receiving portion 9 is flared rearwards. Alternatively, the end portion may have a corresponding, radially internal bevelled edge.

The use of the device will be explained below with reference to FIGS. 4-10, where the free end portion 15 of the first organ 14 will be connected to a side or middle portion of a second organ 16.

The first organ 14 is initially passed through the internal element 1 from the rear end 6 of the element 1 and out through the front end 4 of the element 1 until the end portion 15 of the organ 14 protrudes through this front end 4, whereupon the organ's end portion 15 is everted round the second end 4 as mentioned above.

An aperture 17, which has been or may be formed in such a manner that it has a diameter corresponding to the diameter of the receiving portion 9 of the internal element, is then provided in a side portion of the second organ 16, thus enabling the gripping parts 12 of the external element to be inserted in the aperture 17, the diameter between the external terminations 38 thus being smaller than the diameter of the aperture 17. It should be understood that the aperture 17 need not be made by forming a circular aperture, but that the aperture may be made, e.g. by cutting a single axial incision or two intersecting incisions in the second organ 16, the gripping parts 12 being inserted in the aperture by bending aside edge portions or edge flaps of the aperture, with the result that the aperture becomes approximately circular.

After the aperture 17 has been produced, one option is to insert the gripping parts 12 of the external element 2 in the aperture 17, whereupon the front end portion 3 of the internal element 1 carrying the everted portion 15 of the first organ 14 is inserted in the external element 2 in the forward direction and via its rear end portion 9. When the internal element 1 hereby meets the fingers' slanting main portion 37, the gripping parts 12 are pushed radially and preferably elastically outwards and caused to overlap axially with and abut against or engage with an edge portion 39 of the aperture 17 on the inside of the second organ 16. The gripping parts 12 are thereby locked, and in this locked position thereby prevent the external element 2 from being retracted from the aperture 17.

This option for interconnection of the elements and the organs is encumbered with the disadvantage that the external element 2 must be held in one hand in a specific, spatial position, wherein the gripping parts 12 are located in the second organ 16 while at the same time the internal element 1 must be held in the other hand and inserted in the external element 2.

As a second option, therefore, the front end portion 3 of the internal element 1 carrying the everted portion 15 of the first organ 14 can be only partially inserted in the external element 2 in the forward direction and via its rear end portion 9, thus enabling the two elements 1, 2 to be handled as an assembly, but without the gripping parts 12 being pushed radially outwards. This assembly can then be moved towards the second organ 16 with only one hand, while the gripping parts 12 of the external element 2 are inserted in the aperture 17, whereupon the internal element 2 is pushed completely into the external element, with the result that the gripping parts 12 are pushed radially outwards and caused to overlap axially with and abut against or engage with the edge portion 39 of the aperture 17 on the inside of the second organ 16.

Figure 9:
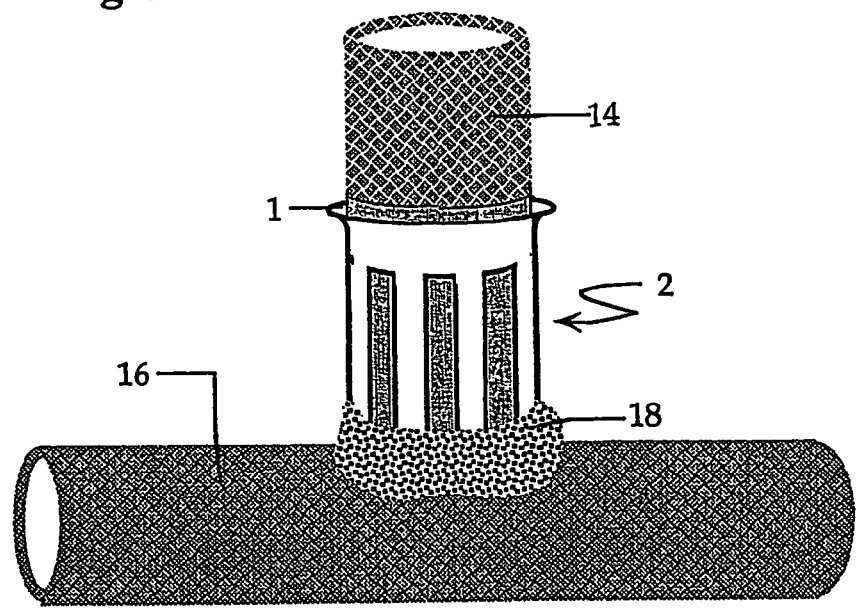
FIG. 9 is a perspective view resembling that illustrated in FIG. 8, but where an adhesive has been applied at the point of connection between the organs.

Finally, an adhesive may be applied to the location for the interconnection of the organs as illustrated in FIG. 9, the adhesive simultaneously providing a seal between the organs and an interconnection of the organs and possibly the elements.

Figure 10:
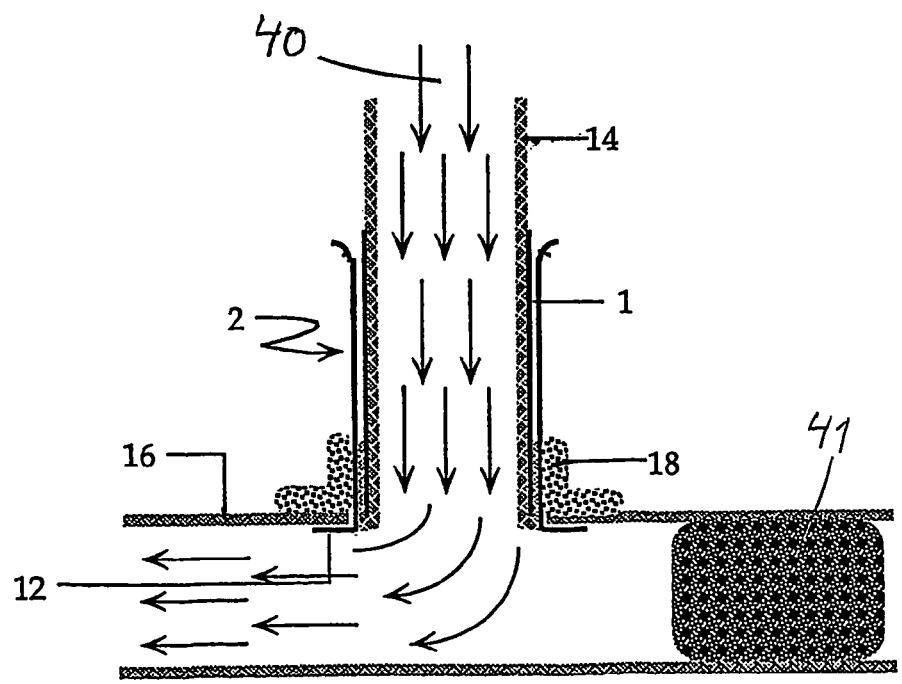
FIG. 10 illustrates a longitudinal section through the components illustrated in FIG. 9.

FIG. 10 illustrates that a fluid 40, such as blood, can flow through the first organ 14, via the elements 1 and 2, into the external element 2, where the fluid can be caused to flow in a desired direction due to the fact that in a portion of the second organ 16, e.g. before the insertion of the external element 2, a sealing plug 41 has been inserted.

Figure 11:
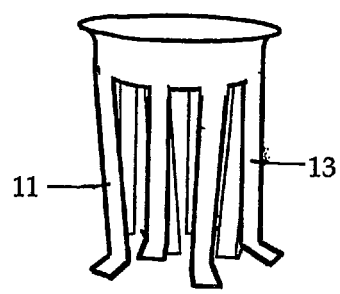
FIG. 11 is a perspective view of a third embodiment of the external element.

FIG. 11 illustrates a third embodiment of the external element, this element having a flared, rear end portion 9.

Figure 12:
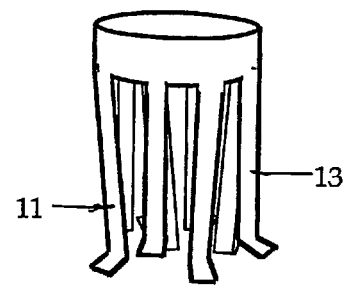
FIG. 12 is a perspective view of a fourth embodiment of the external element.

FIG. 12 illustrates a fourth embodiment of the external element 2, where the rear end portion is cylindrical and may have a bevelled edge.

Figure 13:
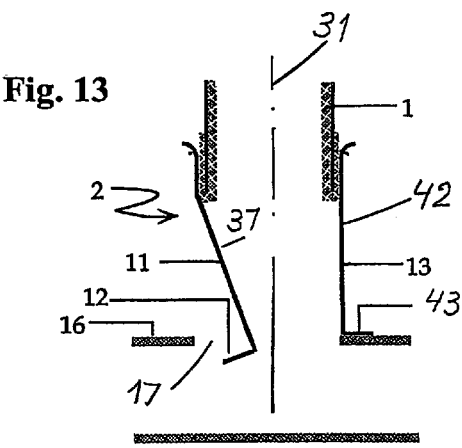
FIG. 13 illustrates a simplified longitudinal section through an internal element with a first organ that has been partially inserted in an external element of the third embodiment, which in turn has been inserted in an aperture in a second organ.

Both these last-mentioned embodiments of element 2 have first fingers 11 as described above in connection with the first and second embodiments of the external element 2. In addition, second fingers 13 are provided along the front edge of the first end portion 9 and between adjacent, first fingers 11. As illustrated in FIG. 13, a main portion 42 of the second fingers 13 extends axially and has at its front end support hooks or support parts 43 which are angled or bent at an angle relative to the main portion 42. The support parts 43 thereby remain located radially outside an axial extension of the receiving portion 9 of the external element 2.

Figure 14:
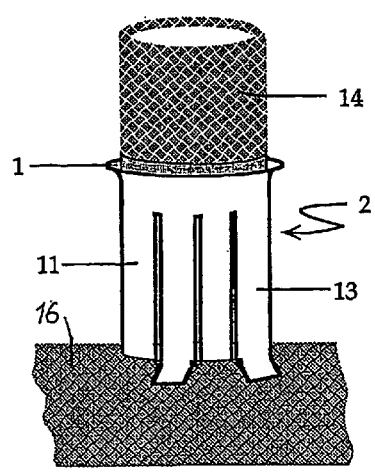
FIG. 14 is a view corresponding to that illustrated in FIG. 13, but where the internal element has been inserted completely in the external element and the components are shown in perspective.
Figure 15:
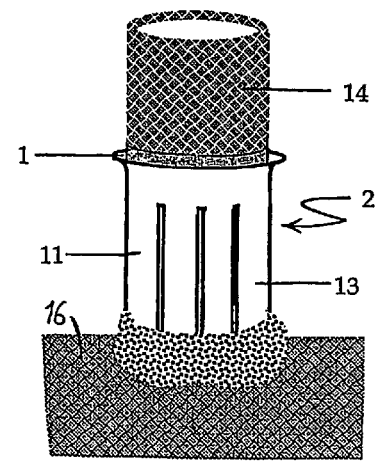
FIG. 15 is a perspective view corresponding to that illustrated in FIG. 14, where an adhesive has been applied at the point of connection between the organs.

The use of these elements will be described with reference to FIGS. 13, 14 and 15. As described above, the first organ 14 is initially inserted in the internal element 1 and everted around front edge 4 thereof, and in the second organ 16 an aperture 17 is provided. The front portion of the second element 2 is then inserted in the aperture 17 until the gripping parts 12 are located inside the second organ 16 and the support parts 13 have come into abutment against or engagement with the outside of the aperture's edge portion 39. The internal element 1 is then inserted in the external element 2 in the same way as that described above, whereby the first fingers 11 are bent radially outwards to abut against the inside of the aperture edge portion 39. If all the fingers are the same length, the aperture edge portion 3 will extend in curves between the gripping parts 12 and the support parts 43. If the second fingers 13 are slightly shorter than the first fingers 11 corresponding to the wall thickness of the second organ 16, the aperture edge portion 39 can extend substantially in one plane. An adhesive 18 can then be provided at the point of connection between the organs 14, 16.

Figure 16:
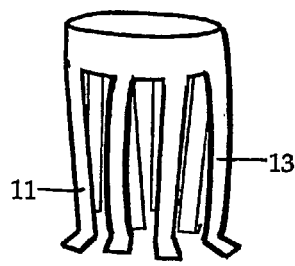
FIG. 16 is a perspective view of a fifth embodiment of the external element.

In FIG. 16 a fifth embodiment of the external element 2 is illustrated, this element 2 resembling the fourth embodiment of the element illustrated in FIG. 12. The difference in this case is that the second fingers 13 are curved, or more specifically provided in a convexly radially outward form. When a force is exerted axially backwards against the support parts 43 while at the same time the receiving portion 9 is secured, the second fingers' main portion 42 may be bent even further. The axial length of the main portion 42 of the second fingers 13 may be slightly larger than the length of the main portion 37 of the first fingers 11.

Figure 17:
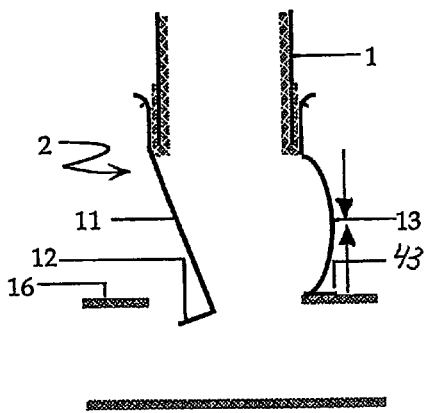
FIGS. 17-19 illustrate three simplified longitudinal sections through an internal element carrying an everted, first organ during three stages of an insertion thereof in an external element of the fifth embodiment, where the external element is inserted in turn into an aperture in the second organ.
Figure 18:
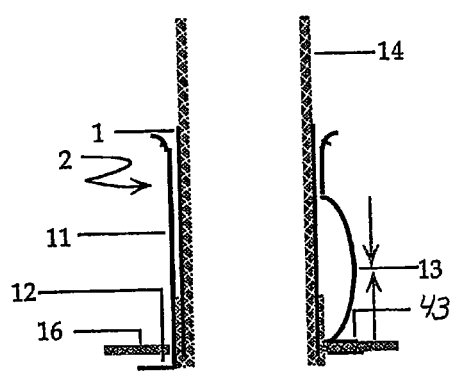
Figure 19:
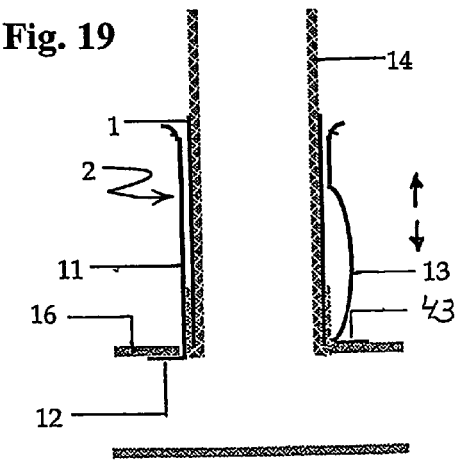

The use of the fifth embodiment of the external element 2 will be described below with reference to FIGS. 17-19. This use corresponds substantially to the use of the third or fourth embodiment of the external element 2.

During a movement of the external element 2 towards the aperture 17 in the second organ 16, the support parts 43, however, may already come into abutment against the outside of the edge portion 39 even before the gripping parts 12 have been moved past the aperture edge portion 39 of the second organ 16.

As the external element 2 continues its movement axially forwards, however, the second organ 16 can exert a force against the support parts 43, with the result that the main portion 42 of the second fingers 13 becomes even more elastically curved to such an extent that the gripping parts 12 can be moved into the second organ 16 and past the aperture edge portion 39. When the internal element 1 together with the first organ 14 are inserted in the external element 2, the first fingers 11 are pushed outwards and on account of the extra curve of the second fingers 13, it is ensured that the gripping parts are located at a distance from the aperture edge portion 39. If the elements 1, 2 are subsequently relaxed, the main portions 42 of the second legs 13 will attempt to straighten out, thereby pulling the gripping portions 12 into abutment against or engagement with the inside of the aperture edge portion 39. The aperture edge portion 39 will thereby be securely held between the gripping parts 12 and the support parts 43.

Figure 20:
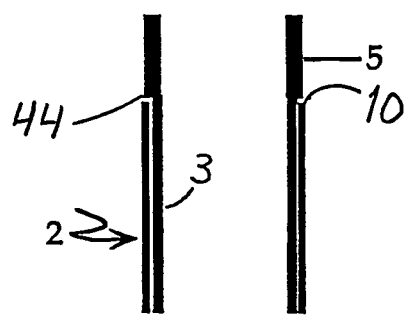
FIG. 20 illustrates a simplified longitudinal section through a second embodiment of the internal element which has been inserted in an external element.

FIG. 20 illustrates a second embodiment of the internal element 1, where it is inserted, e.g., in an external element 2 of the first embodiment.

In this embodiment of the internal element 1, in the external surface of the internal element 1 there are provided, e.g., a circumferential shoulder or abutment surface 44, against which the rear edge 10 of the external element 2 can come into abutment when the internal element 1 has been completely inserted in the external element 2. A correct relative position of the elements 1, 2 is thereby ensured when they have been mounted for an interconnection of two organs 14, 16.

Figure 21:
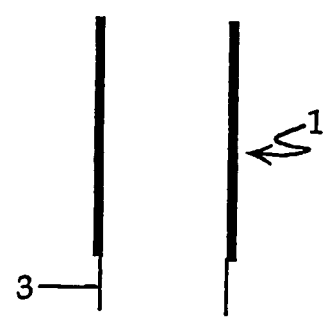
FIG. 21 illustrates a simplified longitudinal section through a third embodiment of the internal element.

As illustrated in FIG. 21, the circumferential shoulder 44 may be obtained by the front portion 3 of the internal element 1 having a smaller outer diameter than the rear portion 5 of the element.

Figure 22:
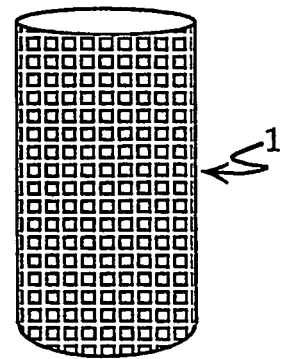
FIG. 22 is a perspective view of a fourth embodiment of the internal element.

FIG. 22 illustrates a fourth embodiment of the internal element 1, where this element is perforated. The weight of the internal element can thereby be reduced. Furthermore, the adhesive 18 can be applied to the external surface of the first organ 14 via the perforation, thus effecting adhesion of the first organ 14 to the internal element 1. The external element 2 may also include a perforation.

Figure 23:
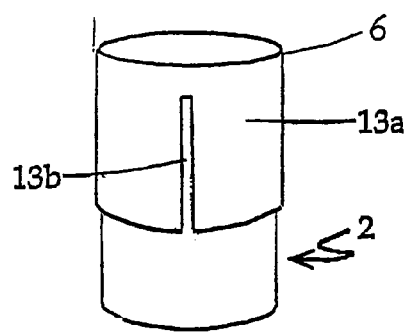
FIG. 23 is a perspective view of a fifth embodiment of the internal element.
Figure 26:
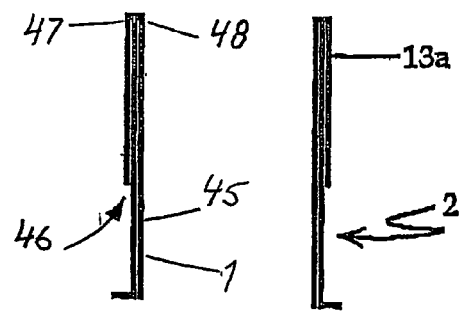
FIG. 26 illustrates a simplified longitudinal section through the elements illustrated in FIG. 25.

FIG. 23 illustrates a fifth embodiment of the internal element 1 comprising an internal portion 45 (FIG. 26) with a shape corresponding to the shape of, e.g., the internal element 1 according to FIG. 1, and a cylindrical, thin-walled, external portion or casing 13a. A rear edge 47 of the casing 13a is secured to a radially opposing rear edge 48 of the internal portion 45, the casing 13a and the internal portion 45 being coaxial and defining an annulus 46.

In the casing 13a there may be provided a slot 13b extending from a front end 49 of the casing 13a for a distance towards the casing's 13a rear end 47.

Figure 24:
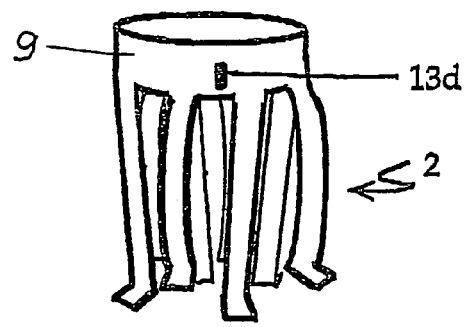
FIG. 24 is a perspective view of a sixth embodiment of an external element.
Figure 25:
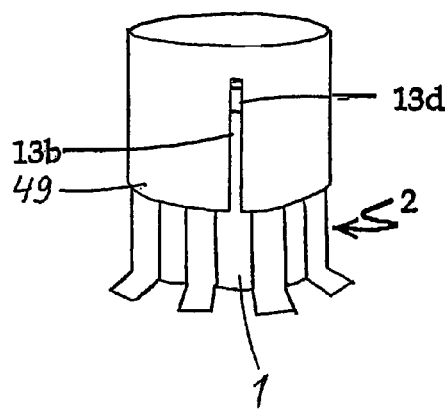
FIG. 25 is a perspective view of an internal element of the fifth embodiment which has been inserted in an external element of the sixth embodiment.

FIG. 24 illustrates a sixth embodiment of the external element 2 which is arranged to cooperate with the internal element according to FIG. 23, and which resembles the fifth embodiment of this element. The receiving portion 9 of the element 2, however, has an outwardly projecting pin or guide pin 13d, whose width considered tangentially relative to the receiving portion 9 is slightly less than the width of the slot 13b.

When inserting the internal portion 45 in the external element 2 and inserting the external element 2 into the annulus 46, the pin 13d can be moved into the slot 13b, thus ensuring a correct, relative angular position of the elements 1, 2. Furthermore, the casing 13a can come into abutment against the outside of the curved fingers 13.

By continuing to insert the internal portion 45 of the external element 1 into the external element 2 and inserting the external element 2 in the annulus 46, a straightening of the curved fingers 13 can be ensured and thereby a clamping of the edge portion 39 of the second organ 16 between the gripping parts 12 and the support parts 43. It will be understood, however, that the first element of the device according to the invention may comprise a casing that is not provided with a slot.

FIGS. 27-29 illustrate this process of joining together these elements 1 and 2 of the fifth and the sixth embodiment respectively. In FIG. 27 the internal portion 45 of the internal element 1 has been inserted in the receiving portion 9 of the external element 2. In FIG. 28 the receiving portion 9 of the external element 2 has been partially inserted in the annulus 46 between the casing 13a and the internal portion 45 of the internal element 1. In FIG. 29 the external element 2 has been completely inserted in the annulus 46 and the second fingers 13 have been straightened out and locked in this position in the annulus 46. In order to ensure a correct relative axial position of the elements 1, 2, the pin 13d can come into abutment against the bottom of the slot 13b. Alternatively, the rear end of the external element 2 can come into abutment against the internal element 1 at the rear boundary of the annulus 46.

FIG. 30 illustrates a seventh embodiment of the external element 2 with alternate straight and curved fingers and with a flared rear portion 9. The main portion of at least two fingers, e.g. the straight fingers 11, has a radially outwardly projecting projection or shoulder 13f (see FIGS. 30-32) which is preferably located near the axial location where the curved fingers' main portions are bent outwards to the greatest extent. The element also comprises a ring or locking collar 13e, whose inner diameter is only slightly larger than the outer diameter of the receiving portion 9, and which is arranged axially movably relative to the receiving portion 9 and the fingers 11, 13. The axial movement backwards and forwards, however, is restricted by the locking collar 13e and the shoulders 13f respectively.

Figure 33:
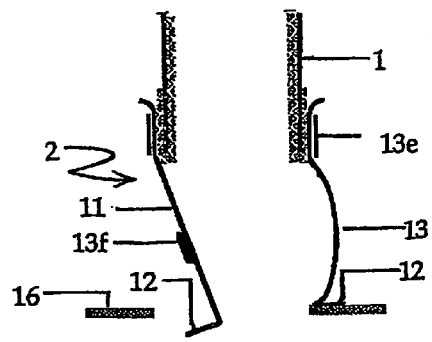
FIGS. 33-35 illustrate three simplified longitudinal sections of the components according to FIGS. 31 and 32 during three respective stages of the connection of two organs.
Figure 34:
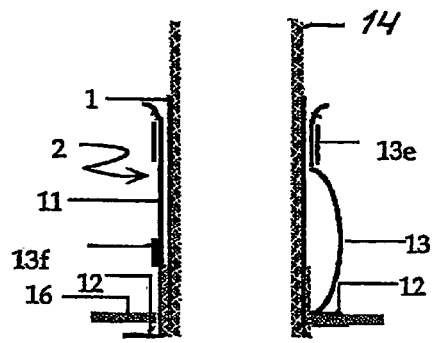
Figure 35:
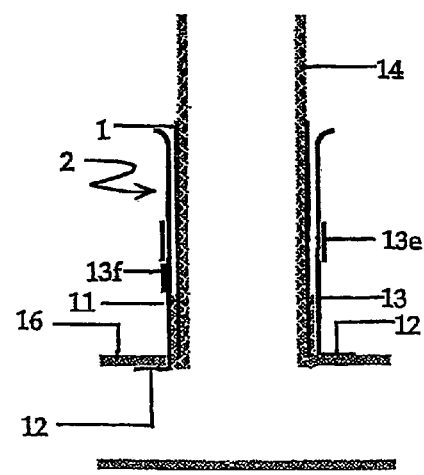

When using the device with an external element 2 of this type, the locking collar 13e is initially mounted radially outside the receiving portion 9 of the internal element 1 and the external element 2 is inserted in an aperture in a second organ 16 (see FIG. 33). The internal element 1 that carries an end portion of a first organ 14 is then inserted in an external element 2 for bending out the first, straight fingers until their gripping claws or parts 12 overlap the aperture edge portion 39 (see FIG. 34). The locking collar 13e is then moved forwards, and when it meets the curved main portions 42, they are straightened out (see FIG. 35). The locking collar 13e thus locks the main portions 42 in the straightened position. The axial length of the curved fingers 13 thereby increases and the gripping parts 12 are pulled into abutment against the inside of the second organ 16, with the result that this organ's aperture edge portion 39 is secured between the gripping parts 12 and the support parts 43.

Figure 36:
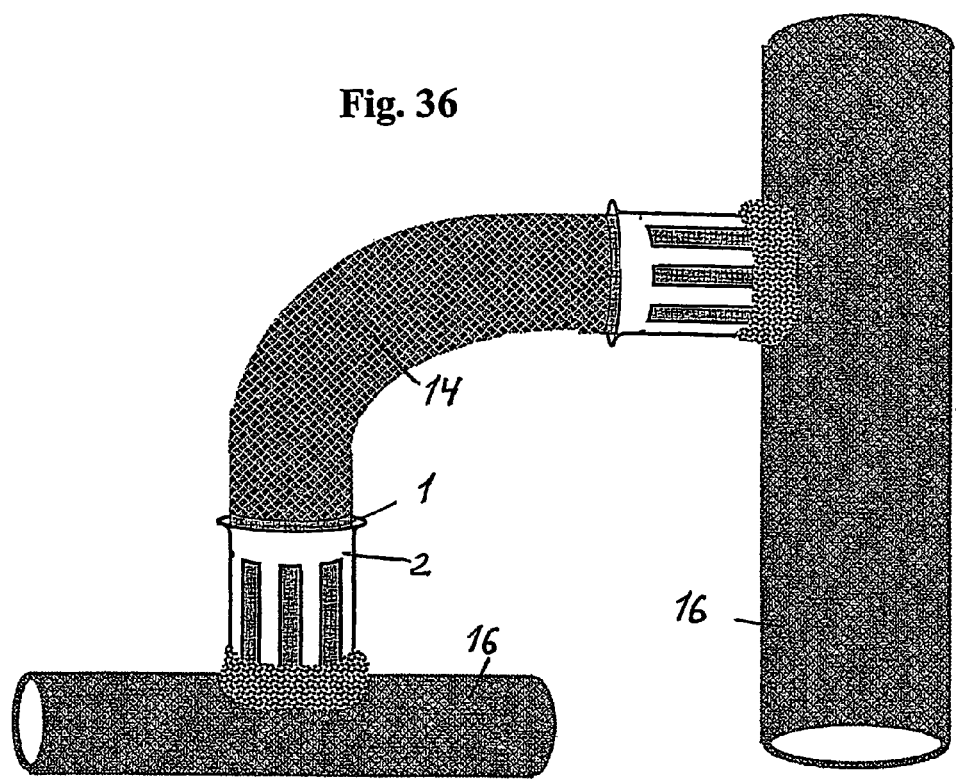
FIG. 36 illustrates an interconnection of side portions of two second organs (side-to-side connection) by means of two devices according to the invention and a first, tubular organ.

FIG. 36 illustrates the use of two devices according to the invention, where two end portions of a first organ are connected to respective side portions of two second organs by means of the devices. The two second organs may hereby have different diameters. Such an interconnection of two second organs 16 may be called a side-to-side connection.

Figure 37:
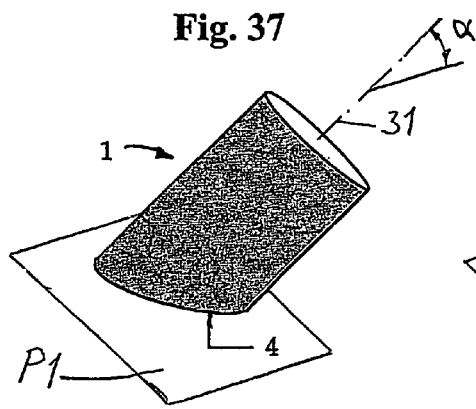
FIG. 37 is a perspective view of a sixth embodiment of an internal element whose front end edge extends slantingly relative to a longitudinal axis of the element.

FIG. 37 is a perspective view of a sixth embodiment of the internal element 1, where the front end edge 4 is located in a first plane P1 that forms a minimal angle α with the element's longitudinal axis 31.

Figure 38:
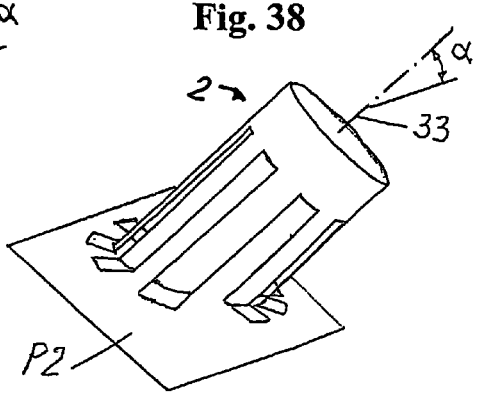
FIG. 38 is a perspective view of an eighth embodiment of the external element, whose front edge portions are located in a front edge plane extending slantingly relative to a longitudinal axis of the element.

FIG. 38 is a perspective view of an eighth embodiment of an external element 2 which is arranged to cooperate with the internal element 1 according to FIG. 37, and whose gripping claws are located in a second plane P2 that forms the same angle α with the external element's longitudinal axis 33.

When using these elements 1, 2, the first organ should preferably be severed so that its front end 4 extends slantingly at an angle α relative to the organ's longitudinal axis. If the cross section of the elements is circular, an elliptical aperture 17 should be cut in the second organ 2. Furthermore, the internal element 1 may preferably comprise a casing with a slot 13b and the external element 2 may comprise a pin 13d as illustrated in FIGS. 23 and 24 respectively in order to obtain a correct relative angular position for the elements when they are joined. If a circular aperture is required in the second organ, however, the elements must have a suitable, elliptical cross section, in which case there is no need for a casing with a slot and an external element with a corresponding pin for a correct relative positioning of the elements, since it is only necessary to ensure that the elements' slanting ends extend substantially in parallel.

Figure 39:
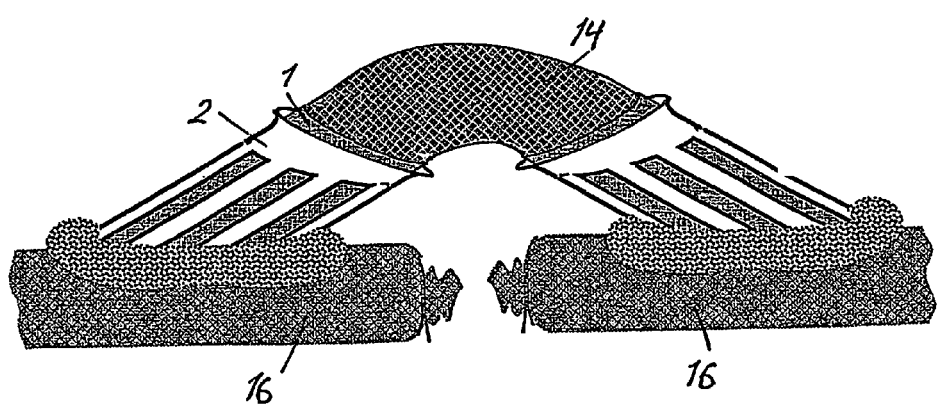
FIG. 39 illustrates an interconnection of side portions of two second organs by means of two elements according to FIGS. 37 and 38 and a first, tubular organ, where the side portions are located near closed ends of the respective second organs (approximate end-to-end connection).

In FIG. 39 a connection is illustrated of two end portions of a first organ 1 with respective side portions of end areas of two second organs 2 by means of the elements according to FIGS. 37 and 38. An approximate end-to-end connection of the second organs 2 and a flow with little fluid resistance can thereby be achieved.

Even though it has been stated above that the first organ 14 can be inserted in the internal element 1, it will be appreciated that the internal element 1 may instead be inserted in the first organ 14. In this case the front edge of the organ may also be everted around the element's front edge. A disadvantage of this is that a rear edge of the first organ 14 may exert a resistance to the fluid flowing in the organ and any particles or the like that are carried along by the fluid may be collected at the edge. In order to reduce this resistance and accumulation, the rear edge may be bevelled. The internal element may also have a flared rear end portion or a bead that contributes to the formation of a corresponding bead on the outside of the first organ 14, where the bead of the first organ may come into abutment in the flared, rear portion of the external element 2 in order to establish the relative axial position of the elements. Furthermore, the internal element may have at its front end a tangentially extending bevel edge, wherein the everted portion of the first organ can be placed, thus ensuring that the everted portion does not impede the fluid flow.

The elements may be made of any kind of suitable material.

Even though it has been stated above that the method and the device according to the invention can be used particularly for interconnection of organs of a body, it will be understood that they can be used in general for interconnection of two tubular objects or organs, generally indicated as organs, provided one organ can be everted as stated above.

The object according to the invention can be employed together with the object of the applicant's international application PCT/NO99/00093.

The invention claimed is:

1. An anastomosis device for interconnection of a first tubular organ to a second tubular organ, the first tubular organ having a first wall, the device comprising:
   (a) a first element with an axially through-going first passage along a first longitudinal axis, a first front end portion, a first front edge, a first rear end portion, and a first rear edge, and
   (b) a second element with an axially through-going second passage along a second longitudinal axis, a second rear end portion or receiving portion, and a second front portion, wherein,
   1) the second front portion is provided with at least two elongated first fingers which are arranged at intervals along the circumference of the second passage, and,
   2) said fingers are of uniform thickness,
   3) each of said fingers is comprised of a main portion extending from the second front portion and in the direction of the second longitudinal axis, and,
   4) said main portion is continuous with a gripping part, wherein the gripping part is directed away from the second longitudinal axis in an undeformed condition of said second element, such that,
   introduction of the first element into the second element displaces the main portions of the fingers radially outwards, and the first element is distanced from the circumference of the second passage such that the wall of the first organ may be accommodated between the first element and the circumference of the second passage.

2. The anastomosis device according to claim 1, wherein the second element is provided with at least one additional, second finger, the second finger being comprised of a main portion, and a support part, such that the second finger is arranged to abut against the outside of the second organ when the gripping parts have been inserted in the second organ.

3. The anastamosis device according to claim 1, wherein the main portion of at least one of the second fingers has a radially outward convex configuration.

4. The anastomosis device according to claim 3, wherein the second element is provided with an annular collar, said collar being movable longitudinally along the outer surface of the second element.

5. The anastomosis device according to claim 4, wherein that at least one finger is provided with a shoulder which protrudes radially outwards from the said finger, such that said shoulder restricts longitudinal mobility of the annular collar.

6. The anastamosis device according to claim 1, wherein the first element is provided with an external sleeve-shaped casing with a front end, said casing being continuous with the first element at the first rear edge, such that the casing and the first element define a cylindrical annulus that stops short of the first front end portion of the first element.

7. The anastamosis device according to claim 6, wherein the casing is provided with a slot which extends from the front end of the casing, and the second element is provided with an outwardly projecting pin, such that said pin engages said slot when the first element is inserted in the second element.

8. The anastamosis device according to claim 1, wherein the first element is provided with a shoulder, such that said shoulder abuts against the second rear end portion of the second element during insertion of the first element in the second element, thereby restricting the depth of insertion of the first element in the second element.

9. The anastamosis device according to claim 1 wherein the second element or the first element or both are perforated.

10. The anastamosis device according to claim 1 wherein that the rear end portion of the second element is flared or bevelled.

11. The anastamosis device according to claim 1, wherein the front edge of the first element defines a first plane and the gripping parts define a second plane, such that the first plane and the second plane form the same angle with respectively the longitudinal axes of the first element and the second element, when the first element is inserted in the second element.

12. The anastamosis device according to claim 1, wherein said fingers gradually progressively incline radially inwardly of said second element.

13. The anastamosis device according to claim 12, wherein said gradual progressive radially inward inclination of said fingers extends over most of the length of the fingers, whereby insertion of said first element into said second element gradually progressively moves said fingers radially outwardly of said second element.

14. An anastomosis device for interconnection of a first tubular blood vessel to a second tubular blood vessel, the first tubular blood vessel having a first wall, the device comprising:
   (a) a first element with an axially through-going first passage along a first longitudinal axis, a first front end portion, a first front edge, a first rear end portion, and a first rear edge, and
   (b) a second element with an axially through-going second passage along a second longitudinal axis, a second rear end portion or receiving portion, and a second front portion, wherein,
   1) the second front portion is provided with at least two elongated first fingers which are arranged at intervals along the circumference of the second passage, and,
   2) said fingers are of uniform thickness,
   3) each of said fingers is comprised of a main portion extending from the second front portion and in the direction of the second longitudinal axis, and,
   4) said main portion is continuous with a gripping part, wherein the gripping part is directed away from the second longitudinal axis in an undeformed condition of said second element, such that,
   introduction of the first element into the second element displaces the main portions of the fingers radially outwards, and the first element is distanced from the circumference of the second passage such that the wall of the first tubular blood vessel may be accommodated between the first element and the circumference of the second passage.

15. The anastomosis device for interconnection of a first tubular blood vessel to a second tubular blood vessel according to claim 14, wherein the second element is provided with at least one additional, second finger, the second finger being comprised of a main portion, and a support part, such that the second finger is arranged to abut against the outside of the second organ when the gripping parts have been inserted in the second tubular blood vessel.

16. The anastomosis device for interconnection of a first tubular blood vessel to a second tubular blood vessel according to claim 15, wherein the main portion of at least one of the second fingers has a radially outward convex configuration.

17. The anastomosis device for interconnection of a first tubular blood vessel to a second tubular blood vessel according to claim 16, wherein the second element is provided with an annular collar, said collar being movable longitudinally along the outer surface of the second element.

18. The anastomosis device for interconnection of a first tubular blood vessel to a second tubular blood vessel according to claim 17, wherein that at least one finger is provided with a shoulder which protrudes radially outwards from the said finger, such that said shoulder restricts longitudinal mobility of the annular collar.

19. The anastomosis device for interconnection of a first tubular blood vessel to a second tubular blood vessel according to claim 14, wherein the first element is provided with an external sleeve-shaped casing with a front end, said casing being continuous with the first element at the first rear edge, such that the casing and the first element define a cylindrical annulus that stops short of the first front end portion of the first element.

20. The anastomosis device for interconnection of a first tubular blood vessel to a second tubular blood vessel according to claim 19, wherein the casing is provided with a slot which extends from the front end of the casing, and the second element is provided with an outwardly projecting pin, such that said pin engages said slot when the first element is inserted in the second element.

* * * * *

UNITED STATES PATENT AND TRADEMARK OFFICE
CERTIFICATE OF CORRECTION

PATENT NO.        : 8,545,524 B2                                                 Page 1 of 1
APPLICATION NO. : 10/522815
DATED             : October 1, 2013
INVENTOR(S)       : Roy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 64 days.

Signed and Sealed this
Fifteenth Day of September, 2015

Michelle K. Lee
*Director of the United States Patent and Trademark Office*